(12) United States Patent
Shah et al.

(10) Patent No.: US 10,772,563 B2
(45) Date of Patent: Sep. 15, 2020

(54) DETECTION OF ELECTRICALLY EVOKED STAPEDIUS REFLEX

(71) Applicant: MED-EL Elektromedizinische Geraete GmbH, Innsbruck (AT)

(72) Inventors: Darshan Shah, Innsbruck (AT); Carolyn Garnham, Matlock (GB); Patrick Hübner, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 122 days.

(21) Appl. No.: 16/079,666

(22) PCT Filed: Feb. 23, 2017

(86) PCT No.: PCT/US2017/019001
§ 371 (c)(1),
(2) Date: Aug. 24, 2018

(87) PCT Pub. No.: WO2017/147221
PCT Pub. Date: Aug. 31, 2017

(65) Prior Publication Data
US 2019/0046116 A1    Feb. 14, 2019

Related U.S. Application Data

(60) Provisional application No. 62/300,119, filed on Feb. 26, 2016.

(51) Int. Cl.
*A61B 5/00* (2006.01)
*A61B 5/11* (2006.01)
(Continued)

(52) U.S. Cl.
CPC .......... *A61B 5/6817* (2013.01); *A61B 5/1104* (2013.01); *A61B 5/12* (2013.01);
(Continued)

(58) Field of Classification Search
CPC ......... A61B 5/1104; A61B 5/12; A61B 5/121; A61B 5/4052; A61B 5/4848; A61B 5/6817; A61N 1/0541; A61N 1/36039
See application file for complete search history.

(56) References Cited

U.S. PATENT DOCUMENTS 5,792,073 A    8/1998  Keefe
6,205,360 B1 *  3/2001  Carter ................ A61N 1/36036
                                                          607/57
(Continued)

FOREIGN PATENT DOCUMENTS

EP    2899996 A1    7/2015

OTHER PUBLICATIONS

International Searching Authority, International Search Report—International Application No. PCT/US17/19001, dated May 15, 2017 together with the Written Opinion of the International Searching Authority, 20 pages.

(Continued)

*Primary Examiner* — Christopher A Flory
(74) *Attorney, Agent, or Firm* — Sunstein LLP

(57) ABSTRACT

Arrangements are described for fitting a cochlear implant to a recipient patient. An acoustic stimulus is delivered to an ear of the patient over a range of acoustic frequencies. A baseline acoustic transfer function resulting from the acoustic stimulus is measured using a response sensor configured to sense pressure response characteristics in the middle ear. And a maximum comfortable level (MCL) of stimulation is determined for at least one stimulation contact in the electrode array, based on performing an electrically evoked measurement to an electric stimulation signal and using the response sensor to measure a modified acoustic transfer function. The modified acoustic transfer function is compared to the baseline acoustic transfer function to determine (Continued)

when a stapedius reflex response occurs and identify the MCL.

15 Claims, 8 Drawing Sheets

(51) Int. Cl.
 *A61B 5/12* (2006.01)
 *A61N 1/36* (2006.01)
 *A61N 1/05* (2006.01)
(52) U.S. Cl.
 CPC .......... *A61B 5/4848* (2013.01); *A61B 5/4851* (2013.01); *A61N 1/0541* (2013.01); *A61N 1/36039* (2017.08); *A61B 5/1107* (2013.01); *A61B 2562/0204* (2013.01); *A61B 2562/0247* (2013.01)

(56) References Cited

U.S. PATENT DOCUMENTS

| | | | | |
|---|---|---|---|---|
| 7,925,355 | B2* | 4/2011 | Quick | A61B 5/121 607/55 |
| 2008/0195179 | A1* | 8/2008 | Quick | A61B 5/121 607/57 |
| 2009/0012580 | A1* | 1/2009 | Arnoldner | A61N 1/36038 607/57 |
| 2009/0018616 | A1* | 1/2009 | Quick | A61B 5/121 607/57 |
| 2010/0145411 | A1* | 6/2010 | Spitzer | A61N 1/36036 607/57 |
| 2011/0082519 | A1* | 4/2011 | Strahl | A61N 1/36036 607/57 |
| 2012/0245655 | A1* | 9/2012 | Spitzer | A61N 1/36036 607/57 |
| 2012/0302859 | A1* | 11/2012 | Keefe | A61B 5/121 600/383 |
| 2013/0079845 | A1* | 3/2013 | Nopp | A61N 1/36039 607/57 |
| 2013/0138180 | A1* | 5/2013 | Kals | A61N 1/36036 607/57 |
| 2014/0100471 | A1* | 4/2014 | Hessler | A61N 1/36039 600/546 |
| 2014/0107441 | A1* | 4/2014 | Grasso | A61B 5/125 600/340 |
| 2014/0323905 | A1* | 10/2014 | Saoji | A61B 5/125 600/554 |
| 2014/0364682 | A1* | 12/2014 | Hillbratt | H04R 25/353 600/25 |
| 2015/0314124 | A1* | 11/2015 | Masaki | A61B 5/12 607/57 |
| 2016/0127840 | A1* | 5/2016 | Hillbratt | H04R 25/353 381/316 |
| 2016/0228357 | A1* | 8/2016 | Lichter | A61K 47/38 |
| 2016/0287870 | A1* | 10/2016 | Yip | A61N 1/36036 |
| 2017/0208403 | A1* | 7/2017 | Nakajima | H04R 25/606 |
| 2017/0215010 | A1* | 7/2017 | Lineaweaver | H04R 25/305 |

OTHER PUBLICATIONS

Lin et al., "Central masking with bilateral cochlear implants," Journal of the Acoustic Society of America, vol. 33, No. 2, pp. 962-969, Feb. 2013.
Voss et al., "Effects of middle-ear disorders on power reflectance measured in cadaveric ear canals," Ear and Hearing, vol. 33, No. 2, 31 pp. 2012.

* cited by examiner

DETECTION OF ELECTRICALLY EVOKED STAPEDIUS REFLEX

This application is a national phase entry of Patent Cooperation Treaty Application PCT/US2017/019001, filed Feb. 23, 2017, which in turn claims priority from U.S. Provisional Patent Application 62/300,119, filed Feb. 26, 2016, both of which are incorporated herein by reference in their entireties.

FIELD OF THE INVENTION

The present invention relates to hearing implant systems, and more specifically, to techniques for detecting electrical stimulation signals in such systems, and the body's response to such signals.

BACKGROUND ART

A normal ear transmits sounds as shown in FIG. 1 through the outer ear 101 to the tympanic membrane 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolus where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, hearing prostheses have been developed. For example, when the impairment is related to operation of the middle ear 103, a conventional hearing aid may be used to provide mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system, including an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110.

Typically, the electrode array 110 includes multiple electrode contacts 112 on its surface that provide selective stimulation of the cochlea 104. Depending on context, the electrode contacts 112 are also referred to as electrode channels. In cochlear implants today, a relatively small number of electrode channels are each associated with relatively broad frequency bands, with each electrode contact 112 addressing a group of neurons with an electric stimulation pulse having a charge that is derived from the instantaneous amplitude of the signal envelope within that frequency band.

It is well-known in the field that electric stimulation at different locations within the cochlea produce different frequency percepts. The underlying mechanism in normal acoustic hearing is referred to as the tonotopic principle. In cochlear implant users, the tonotopic organization of the cochlea has been extensively investigated; for example, see Vermeire et al., *Neural tonotopy in cochlear implants: An evaluation in unilateral cochlear implant patients with unilateral deafness and tinnitus*, Hear Res, 245(1-2), 2008 Sep. 12 p. 98-106; and Schatzer et al., *Electric-acoustic pitch comparisons in single-sided-deaf cochlear implant users: Frequency-place functions and rate pitch*, Hear Res, 309, 2014 March, p. 26-35 (both of which are incorporated herein by reference in their entireties).

In some stimulation signal coding strategies, stimulation pulses are applied at a constant rate across all electrode channels, whereas in other coding strategies, stimulation pulses are applied at a channel-specific rate. Various specific signal processing schemes can be implemented to produce the electrical stimulation signals. Signal processing approaches that are well-known in the field of cochlear implants include continuous interleaved sampling (CIS), channel specific sampling sequences (CSSS) (as described in U.S. Pat. No. 6,348,070, incorporated herein by reference), spectral peak (SPEAK), and compressed analog (CA) processing.

For an audio prosthesis such as a cochlear implant to work correctly, some patient-specific operating parameters need to be determined in a fit adjustment procedure where the type and number of operating parameters are device dependent and stimulation strategy dependent. Possible patient-specific operating parameters for a cochlear implant include:

$THR_1$ (lower detection threshold of stimulation amplitude) for Electrode 1
$MCL_1$ (maximum comfortable level) for Electrode 1
Phase Duration for Electrode 1
$THR_2$ for Electrode 2
$MCL_2$ for Electrode 2
Phase Duration for Electrode 2
. . .
Pulse Rate (may be also channel dependent)
Number of fine structure channels
Compression
Parameters of frequency->electrode mapping
Parameters describing the electrical field distribution FIG. 2 shows a block diagram of a cochlear implant fitting system configured to perform such post-implantation fitting. Control Unit 201 for Recording and Stimulation, for example, a Med-El Maestro Cochlear Implant (CI) system, generates stimulation signals and analyzes response measurements. Connected to the Control Unit 201 is an Interface Box 202, for example, a Diagnostic Interface System such as the DIB II conventionally used with the Maestro CI system that formats and distributes the input and output signals between the Control Unit 201 and the system components implanted in the Patient 206. For example, as shown in FIG. 2, there may be an Interface Lead 203 connected at one end to the Interface Box 202 and at the other end having Electrode Plug 207 that then divides into a Cochlear Implant Electrode 204 and an Extra-Cochlear Ground Electrode 205. After delivering a stimulation pulse, a Cochlear Implant Electrode 204 may be used as a sensing element to determine current and voltage characteristics of the adjacent tissue.

One common method for fit adjustment is to behaviorally find the threshold (THR) and maximum comfortable level (MCL) value for each separate electrode contact. See for example, Rätz, *Fitting Guide for First Fitting with MAE-STRO 2.0*, MED-EL, Fürstenweg 77a, 6020 Innsbruck, 1.0 Edition, 2007. AW 5420 Rev. 1.0 (English_EU); incorporated herein by reference. Other alternatives/extensions are sometimes used with a reduced set of operating parameters; e.g. as suggested by Smoorenburg, *Cochlear Implant Ear Marks*, University Medical Centre Utrecht, 2006; and U.S. Patent Application 20060235332; which are incorporated herein by reference. Typically each stimulation channel is fitted separately without using the information from already fitted channels. The stimulation current on a given electrode typically is increased in steps from zero until the MCL or THR is reached.

FIG. 3 shows a portion of the middle ear anatomy in greater detail, including the incus 301 and the stapes 302. The lenticular process end of the incus 301 vibrates the head 305 of the stapes 302, which in turn vibrates the base 303 of the stapes 302 which couples the vibration into the inner ear (cochlea). Also connected to the head 305 of the stapes 302 is the stapedial tendon 306 of the stapedius muscle situated within the bone of the pyramidal eminence 307. When a loud noise produces an excessively high sound pressure that could damage the inner ear, the stapedius muscle reflexively contracts to decrease the mechanical coupling of the incus 301 to the stapes 302 (and thereby also reduce the force transmission). This protects the inner ear from excessively high sound pressures.

The tensing of the stapedius muscle when triggered by such high sound pressures is also referred to as the stapedius reflex. Medically relevant information about the functional capability of the ear may be obtained by observation of the stapedius reflex. Measurement of the stapedius reflex also is useful for setting and/or calibrating cochlear implants because the threshold of the stapedius reflex is closely correlated to the psychophysical perception of comfortable loudness, the so-called maximum comfortable level (MCL), determined in the fitting process described above.

The stapedius reflex can be determined in an ambulatory clinical setting using an acoustic tympanometer that measures the changes in acoustic impedance of the middle ear caused by stapedial muscle contraction in response to loud sounds. The stiffness of the vibrating elements of a middle ear (also called the compliance) is increased when the stapedius reflex has been elicited. During tympanometry measurements, the outer ear canal is tightly closed by a plug device to define a closed air space between the plug and the tympanic membrane. A tube in the plug provides air from an air pump that is adapted to vary the air pressure within the closed air space relative to the pressure in the middle ear of the patient. The plug also provides a sound source, e.g. a loudspeaker, that is adapted to provide a sound towards the tympanic membrane, and a sensor, e.g. a microphone, that is adapted to sense a reflected portion of the sound provided by the sound source that is reflected from the tympanic membrane. But performing these tests and measurements is rather difficult and requires quite specialized equipment, high skill levels and significant time from the fitting audiologist, as well as full cooperation of the patient.

To measure the stapedius reflex intra-operatively, it also is known to use electrodes that are brought into contact with the stapedius muscle to relay to a measuring device the action current and/or action potentials generated, e.g. a measured EMG signal, upon a contraction of the stapedius muscle. But a reliable minimally-invasive contact of the stapedius muscle is difficult because the stapedius muscle is situated inside the bony pyramidal eminence and only the stapedial tendon is accessible from the interior volume of the middle ear.

Various intraoperative stapedius muscle electrodes are known from U.S. Pat. No. 6,208,882 (incorporated herein by reference in its entirety), however, these only achieve inadequate contact of the stapedius muscle tissue (in particular upon muscle contraction) and are also very traumatizing. This reference describes one embodiment that uses a ball shape monopolar electrode contact with a simple wire attached to it. That would be very difficult to surgically position into a desired position with respect to the stapedius tissue and to fix it there allowing for a long-term atraumatic and stable positioning. Therefore the weakness of this type of electrode is that it does not qualify for chronic implantation. In addition, there is no teaching of how to implement such an arrangement with a bipolar electrode with electrode contacts with sufficient space between each other to enable bipolar registration.

Some intraoperative experiments and studies have been conducted with hook electrodes that have been attached at the stapedius tendon or muscle. These electrode designs were only suitable for acute intra-operative tests. Moreover, some single hook electrodes do not allow a quick and easy placement at the stapedius tendon and muscle—the electrode has to be hand held during intra-operative measurements, while other double hook electrodes do not ensure that both electrodes are inserted into the stapedius muscle due to the small dimensions of the muscle and the flexibility of the electrode tips. One weakness of these intraoperative electrodes is that they do not qualify for chronic implantation.

German patent DE 10 2007 026 645 (incorporated herein by reference in its entirety) discloses a two-part bipolar electrode configuration where a first electrode is pushed onto the stapedius tendon or onto the stapedius muscle itself, and a second electrode is pierced through the first electrode into the stapedius muscle. One disadvantage of the described solution is its rather complicated handling in the very limited space of the surgical operation area, especially manipulation of the fixation electrode. In addition, the piercing depth of the second electrode is not controlled so that trauma can also occur with this approach. Also it is not easy to avoid galvanic contact between both electrodes.

U.S. Patent Publication 20100268054 (incorporated herein by reference in its entirety) describes a different stapedius electrode arrangement having a long support electrode with a base end and a tip for insertion into the target tissue. A fixation electrode also has a base end and a tip at an angle to the electrode body. The tip of the fixation electrode passes perpendicularly through an electrode opening in the support electrode so that the tips of the support and fixation electrodes penetrate into the target tissue so that at least one of the electrodes senses electrical activity in the target stapedius tissue. The disadvantages of this design are analogous to the disadvantages mentioned in the preceding patent.

U.S. Patent Publication 20130281812 (incorporated herein by reference in its entirety) describes a double tile stapedial electrode for bipolar recording. The electrode is configured to be placed over the stapedius tendon and a sharp tip pierces through the bony channel towards the stapedius muscle. The downside of this disclosure is again its rather complicated handling in the very limited space of the surgical operation area, Various other stapedial electrode designs also are known, all with various associated drawbacks; for example, US 2011/0255731, US 2014/0100471, U.S. Pat. Nos. 8,280,480, and 8,521,250, all incorporated herein by reference in their entireties. A simple wire and ball contact electrode is very difficult to surgically position and to keep it atraumatically stabilized for chronic implantations. The penetrating tip of such a design must be stiff enough to pass through the bone tunnel, but if the tip is too stiff, it is difficult to bend and maneuver the wire into its position. And some stapedius muscle electrode designs are only monopolar electrodes (with a single electrode contact) and are not suitable for a bipolar arrangement with the electrode contacts with sufficient distance between each other to enable bipolar registration. Finally, another design is disclosed in co-pending U.S. Provisional Patent Application 62/105,260 (incorporated herein by reference in its entirety).

SUMMARY OF THE INVENTION

Embodiments of the present invention are directed to methods, systems and computer program products for fitting a cochlear implant to a recipient patient. An acoustic stimulus is delivered to an ear of the patient over a range of acoustic frequencies. A baseline acoustic transfer function of the acoustic stimulus is measured using a response sensor configured to sense pressure response characteristics in the middle ear; for example, a response of a microphone to a steady sound level or to environmental sound. And a maximum comfortable level (MCL) of stimulation is determined for at least one stimulation contact in the electrode array, based on performing an electrically evoked measurement comprising: i. delivering an electric stimulation signal at a given stimulus intensity to the at least one stimulation contact, ii. using the response sensor to measure an modified acoustic transfer function to the electric stimulation signal, iii. comparing the modified acoustic transfer function to the baseline acoustic transfer function to determine when a stapedius reflex response occurs, iv. when the stapedius reflex response does not occur, increasing the stimulus intensity and repeating the electrically evoked measurement, and v. when the stapedius reflex response occurs, identifying the MCL for the at least one stimulation contact based on the corresponding stimulus intensity.

In further specific embodiments, the response sensor may be configured to sense the pressure response characteristics in the free space, for example, using a sensing microphone, or within the ossicular chain, e.g. using a pressure sensor or a microphone as disclosed, for example, in U.S. Patent Publication 2005113633, U.S. Patent Publication 20140100415, or U.S. Patent Publication 20110144415, all of which are incorporated herein by reference in their entireties. And the pressure response characteristics may include sound level and frequency response.

DETAILED DESCRIPTION OF SPECIFIC EMBODIMENTS

Embodiments of the present invention are based on the use of a response sensor (e.g. a sensing microphone or pressure sensor) located in the middle or inner ear to detect an electrically evoked stapedius reflex response in cochlear implant recipients. Unlike with a conventional tympanometer, which measures compliance, embodiments of the invention detect stapedius reflex events based on subtle fluctuations in the pressure response in the middle ear, the static pressure or sound pressure amplitude, phase and/or frequency response. And unlike with tympanometry measurements, no closure of the outer ear is required and no static ear canal pressure changes by a connected air pump are needed.

It is known that when the stapes is fixed by dental cement in a cadaver, there is normally a frequency dependent change in the power of sound reflected back from the tympanic membrane (e.g., from Voss et al., "Effects of Middle-Ear Disorders on Power Reflectance Measured in Cadaveric Ear Canals," *Ear and Hearing* 33.2 (2012): 195-208; incorporated herein by reference in its entirety). During the reflex, the sound inside the free space of the middle ear will also have an altered transmission characteristic (i.e. an altered acoustic transfer function). But the level and frequency dependence of the latter effect is expected to be complex since the movements of the tympanic membrane are complicated and the various surrounding acoustic compliances also change. In addition, there will be significant variations between individual patients. To some extent, the reproducibility of the measurement may be improved by averaging multiple reflex response measurements.

The foregoing considerations suggest that it may be useful to measure, during the application of an external acoustic stimulus, the change in the response characteristics of the response sensor during and after the electrically evoked acoustic reflex over a range of frequencies, and to compare the spectra acoustic transfer function with that obtained without any electrical stimulation. The differences in the obtained intensity levels and/or spectra would signify the presence of the stapedius reflex. The external acoustic stimulus should be present before, during, and after the application of the electric stimulus, which evokes the acoustic reflex, and the acoustic stimulus itself must not elicit the acoustic reflex. The according signature of the acoustic reflex in the signal of the response sensor is expected to be very small, well within the noise level of the sensed acoustic stimulus. In addition, the signature of the acoustic reflex in the response signal is expected to be a slow variation compared to e.g. a 3 kHz acoustic stimulus signal. The acoustic reflex may also be measurable without the presence of an acoustic stimulus, but in this case one cannot take advantage from the comparison and analysis of the recorded spectra.

Figure 4:
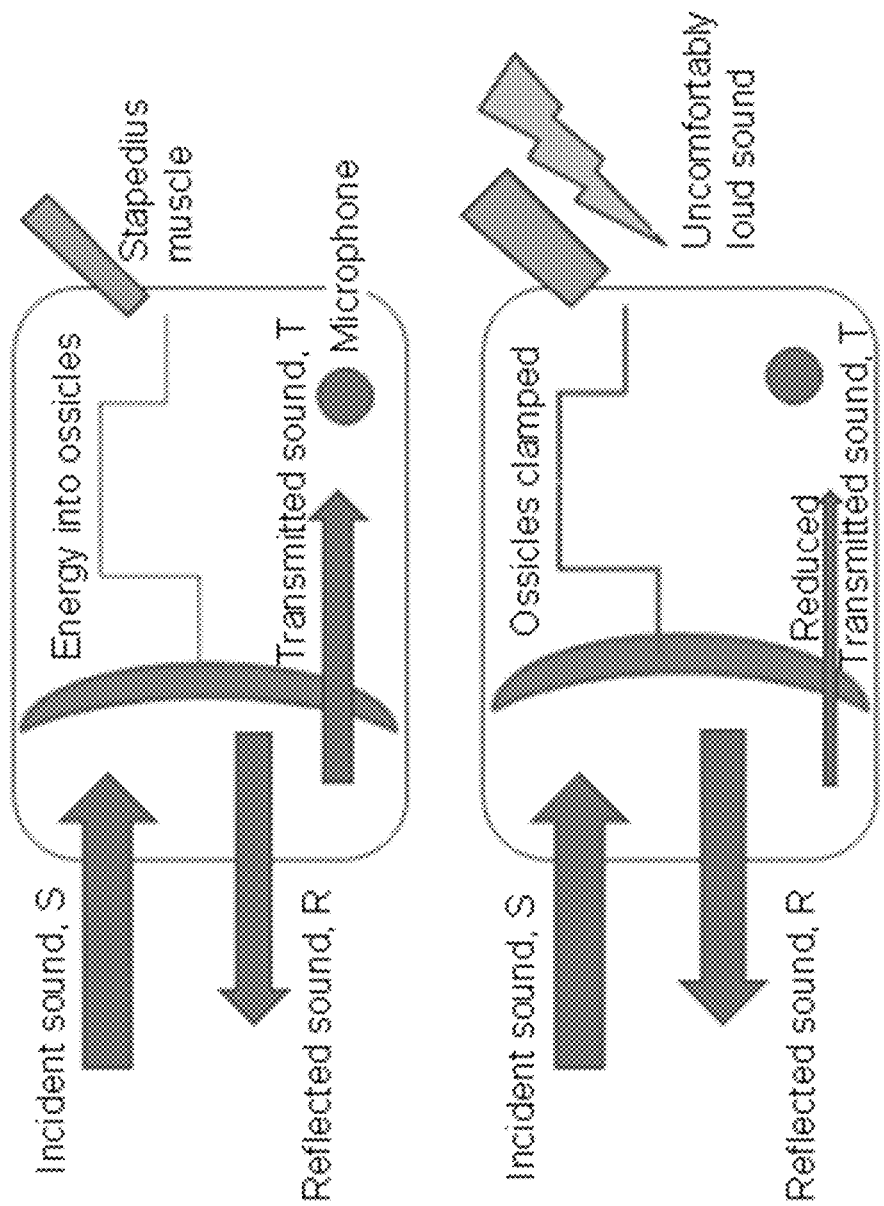
FIG. 4 illustrates the operating principal of embodiments of the present invention.

FIG. 4 illustrates the operating principle of the present invention, showing how changes in transmitted sound level can be used to detect a stapedius reflex response. It is known from tympanometry measurements that during the stapedius reflex, the acoustic compliance of the tympanic membrane is reduced and more sound is reflected back into the outer canal. So as seen in the top portion of FIG. 4, for sounds in the normal range of loudness, the stapedius muscle is relaxed, and the sound energy S incident on the tympanic membrane is split into a reflected portion R and a transmitted portion T, S=R+T. The transmitted portion is a sum of a portion transmitted through the ossicle chain $T_O$ and another portion transmitted through the free air space of the middle ear $T_A$. As shown in the bottom portion of FIG. 4, for sounds that are uncomfortably loud, the stapedius reflex response contracts the stapedius muscle, clamping the ossicles in the middle ear, reflecting more sound back from the tympanic membrane into the outer ear canal and transmitting less sound across the tympanic membrane into the middle ear through the ossicle chain $T_O$ and the free air space of the middle ear $T_A$. The relative dominance of the middle ear transmission channels is likely to be frequency and pathology dependent. Furthermore, there also will be sound transmitted into the middle ear through bone conduction, which will not change significantly. Contrary to conventional tympanometry where the changed vibrational properties of the tympanic membrane in response to the elicitation of a stapedius reflex can be determined by a single quantity (i.e. R), embodiments of the present invention instead analyse one partial component of the transmitted portion in the middle ear, i.e. either $T_A$ or $T_O$, using a frequency and/or level dependent algorithm.

Figure 1:
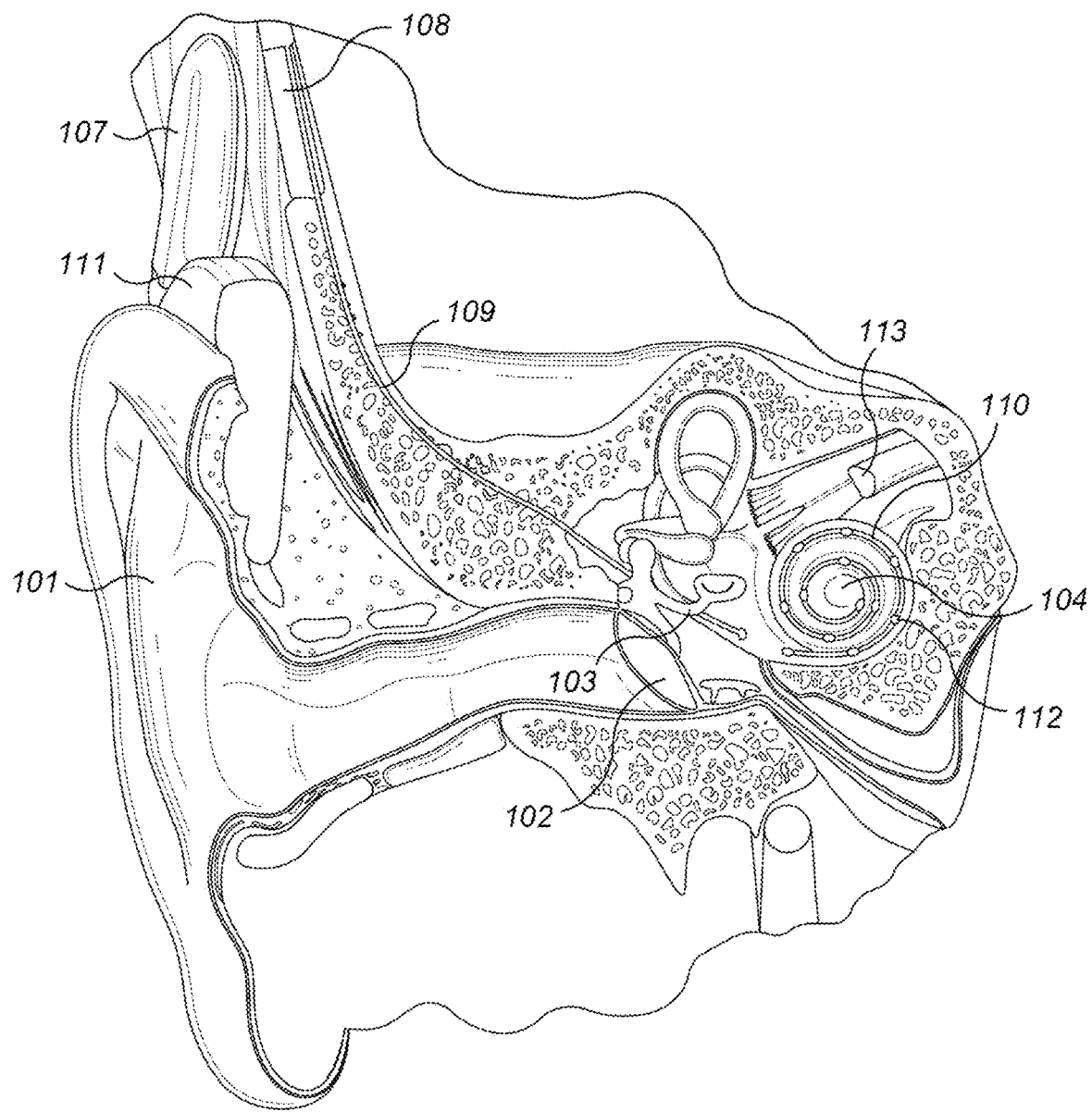
FIG. 1 shows anatomical structures in a human ear having a cochlear implant system.
Figure 2:
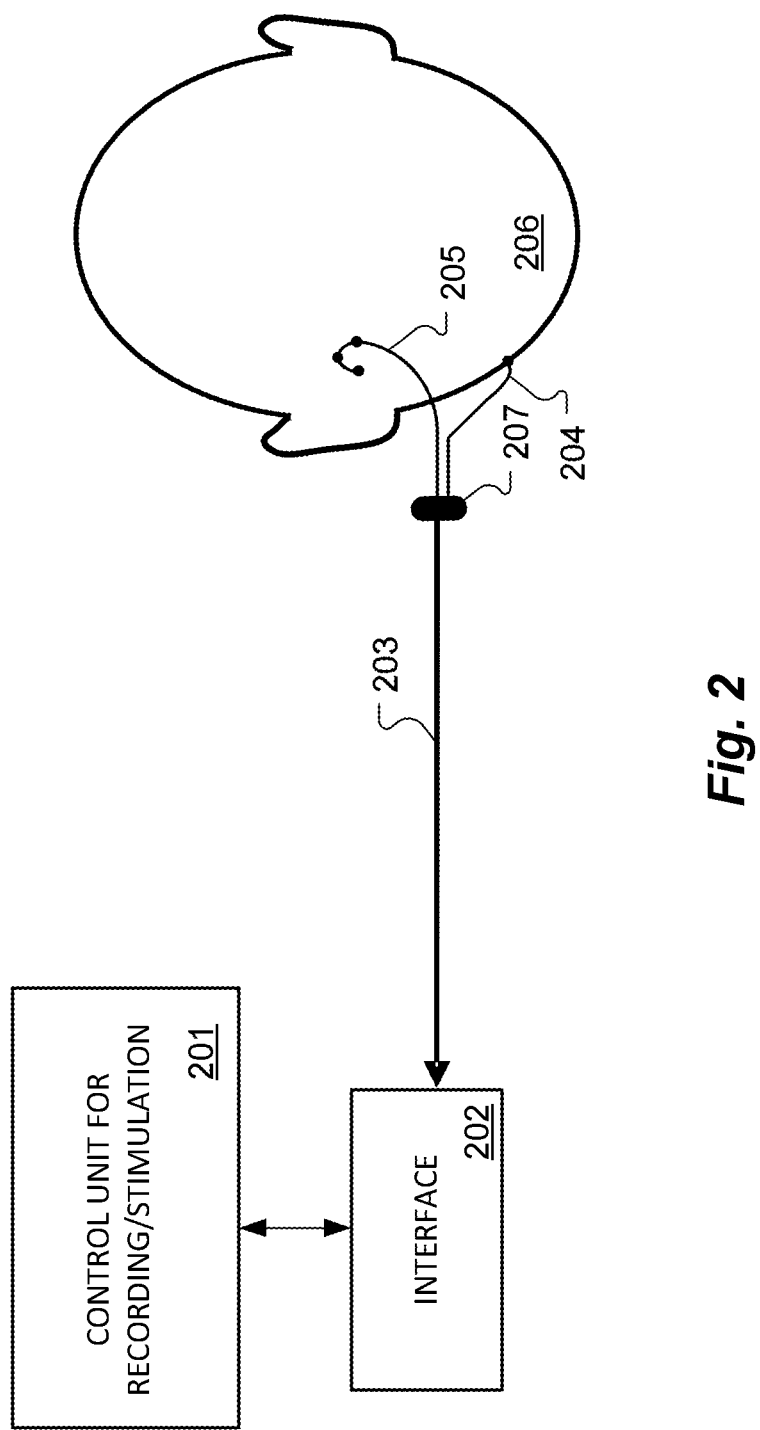
FIG. 2 shows a block diagram of a cochlear implant fitting system configured to perform a conventional post-implantation fitting.
Figure 3:
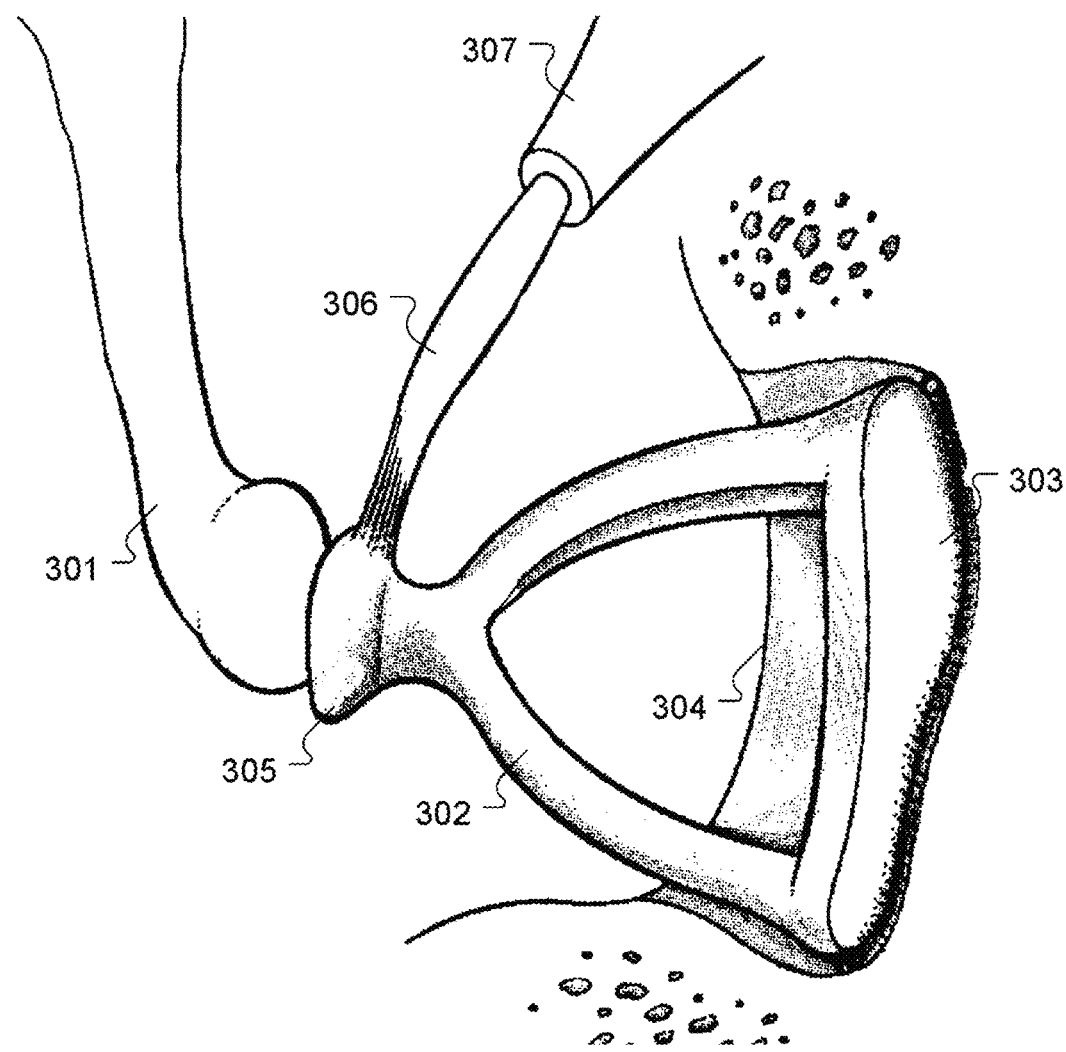
FIG. 3 shows a portion of the middle ear anatomy in greater detail.
Figure 5:
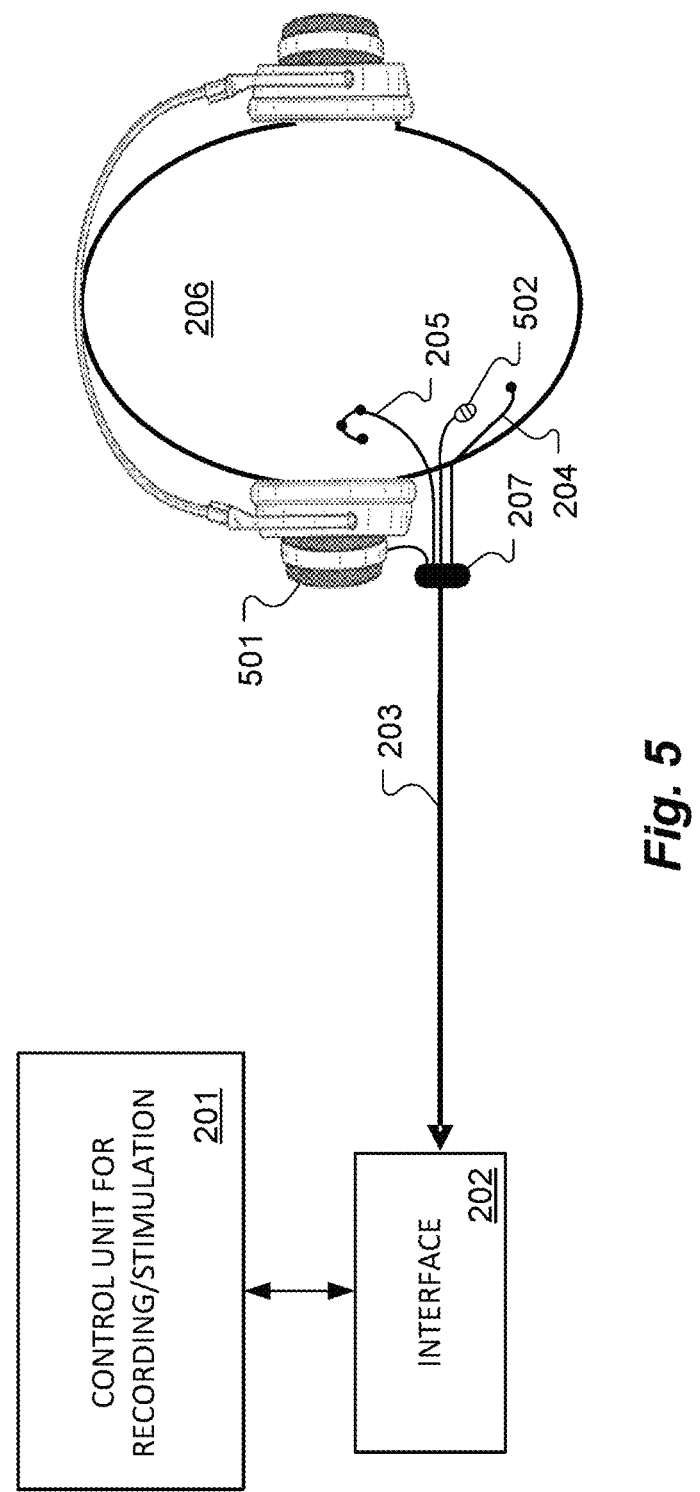
FIG. 5 shows a block diagram of a cochlear implant fitting system configured to perform a post-implantation fitting according to an embodiment of the present invention.

FIG. 5 shows a block diagram of a cochlear implant fitting system configured to perform a post-implantation fitting according to an embodiment of the present invention. The embodiment shown in FIG. 5 is based on the conventional fitting system shown in FIG. 2, and further includes an additional external sound source, e.g. a simple External Speaker 501 (e.g., headphones or a conventional loudspeaker) that produces a defined sound of adequate level such that the change in the middle ear sound characteristics during the electrically evoked stapedius reflex response will be detectable by the additional Middle Ear Sensor 502 such as a microphone or pressure sensor. Then circuitry and algorithms in the rest of the fitting system (e.g. Control Unit 201) can calculate and identify the changes in the measurement signals. A pseudo code example of such a method can be developed as:

```
Acoustic Baseline Measurement:
    AcousticBaseline (acous_stim, acous_response)
MCL Determination:
    stim_intensity = threshold_intensity
    While Stap_reflex = false
        Elec_stim (elec_stim_signal, stim_intensity)
        Elec_response (elec_evoked_response)
        Compare_responses (acous_response,
            elec_evoked_response)
        If Stap_reflex=false,
            then stim_intensity = stim_intensity+1
        Else If Stap_reflex=true
            then ident_MCL
```

The details of such an arrangement are set forth in the following discussion.

The Control Unit 201 generates an acoustic stimulus over a range of acoustic frequencies that is delivered via the Interface Box 201 and the Interface Lead 203 by the External Speaker 501 to the affected ear of the Patient 206. In alternative embodiments, instead of the External Speaker 501, ambient sound may be used as the sound source. The Middle Ear Sensor 502 then measures a baseline acoustic transfer function of the acoustic stimulus, sensing the corresponding pressure response characteristics in the middle ear. In some embodiments, rather than sensing the pressure response characteristics in the middle ear, a sensor could measure fluctuations in endolymph or perilymph pressure in the inner ear. Note that the patient is not intended to actually hear the acoustic stimulus, and so its transmission to the cochlear implant signal processor that produces the cochlear implant stimulation signal, should be prohibited during the measurement procedure, so that the cochlear implant Electrode Array 205 does not deliver electrical stimulation signals reflecting the acoustic stimulus. The acoustic transfer function measured by the Middle Ear Sensor 502 is then delivered by the Interface Lead 203 and the Interface Box 201 back to the Control Unit 201.

The Control Unit 201 uses the measured baseline acoustic transfer function (without a simultaneous electrical stimulus via the cochlear implant Electrode Array 205) as the reference basis for determining a maximum comfortable level (MCL) of stimulation for at least one stimulation contact in the Electrode Array 205, based on performing one or more modified acoustic transfer function measurements. The Control Unit 201 generates an electric stimulation signal for a given stimulation contact at a given stimulus intensity, which is delivered via the Interface Box 201 and the Interface Lead 203 by the Electrode Array 205 to the selected stimulation contact. The Middle Ear Sensor 502 then measures a modified acoustic transfer function to the electric stimulus, sensing the corresponding modified pressure response characteristics in the middle ear.

The modified acoustic transfer function measured by the Middle Ear Sensor 502 is then delivered by the Interface Lead 203 and the Interface Box 201 back to the Control Unit 201, which compares the baseline acoustic transfer function to the modified acoustic transfer function to determine when a stapedius reflex response has occurred. The measurements capture changes in the response characteristics (amplitude, phase and/or frequency content) of either static pressure, or of external sound that is transmitted into the free space and the ossicle chain of the middle ear, that occur due to the stapedius reflex response (when the ossicular transmission pathway stiffens). This in turn alters the sound transmission characteristics of the middle ear, as well as the static pressure within the middle ear due to the induced small temporary changes in the volume of the air and fluid spaces. When the Control Unit 201 determines that a stapedius reflex response does not occur, it then increases the electrical stimulus intensity and repeats the electrically evoked measurement for that stimulation contact. When the Control Unit 201 determines that a stapedius reflex response does occur, it identifies the existing stimulus intensity level as corresponding to the MCL for that stimulation contact, and the process may then be repeated for other stimulation contacts.

As mentioned above, the strength of this method is that not a single event in the sensor response is looked for, but that the system can compare whole spectra. Thus, a signature of the acoustic reflex may be identified more reliable, even more as the sensor response induced by the acoustic (or stapedius) reflex is expected to be small to the sensed noise level. The expected low frequency change caused by the acoustic reflex requires a sensor which is sufficiently responsive to low frequency changes.

Figure 6A:
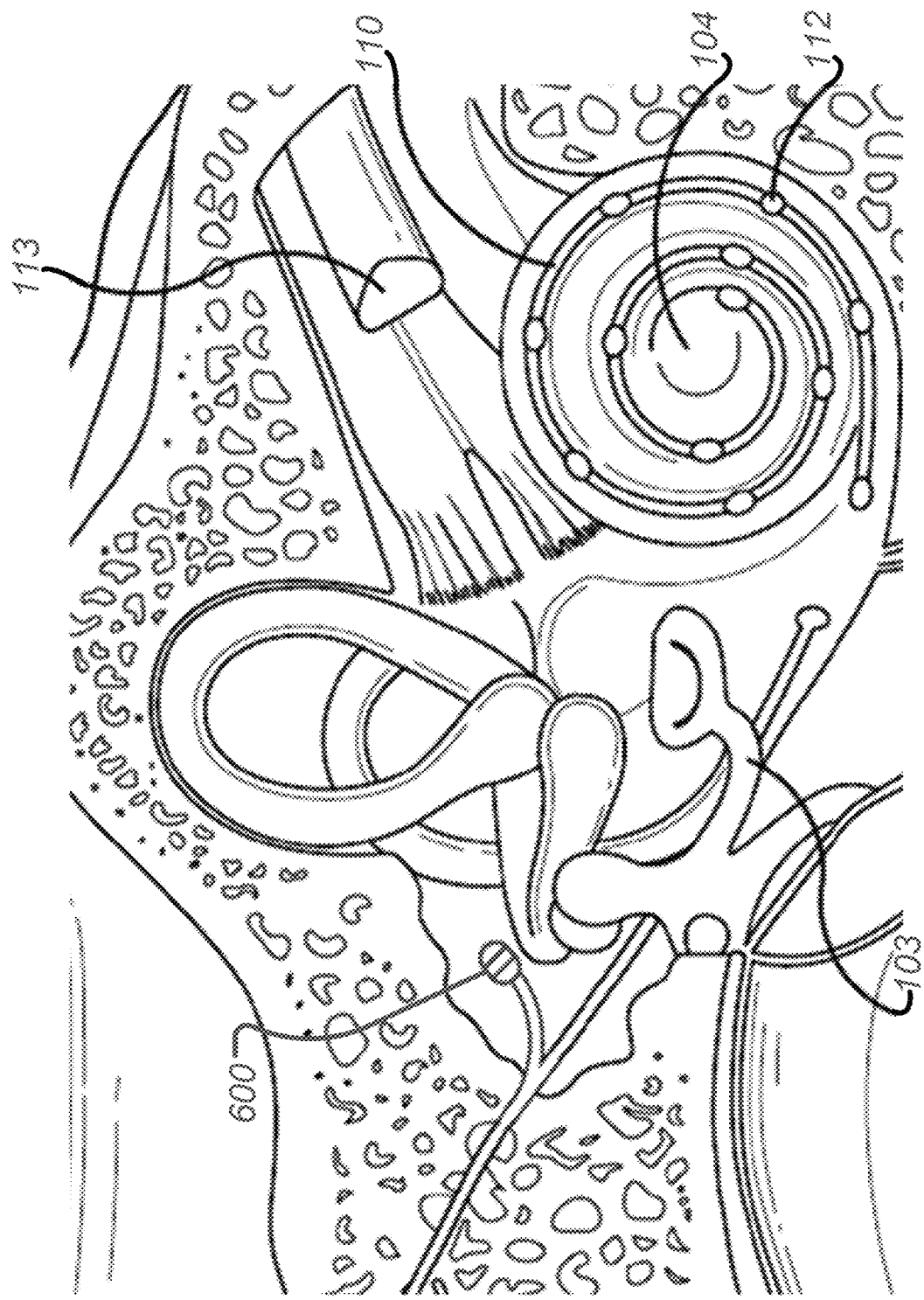
FIG. 6A-6C shows various response sensor arrangements for measuring the stapedius reflex response in the middle ear of a patient with a cochlear implant according to embodiments of the present invention.
Figure 6B:
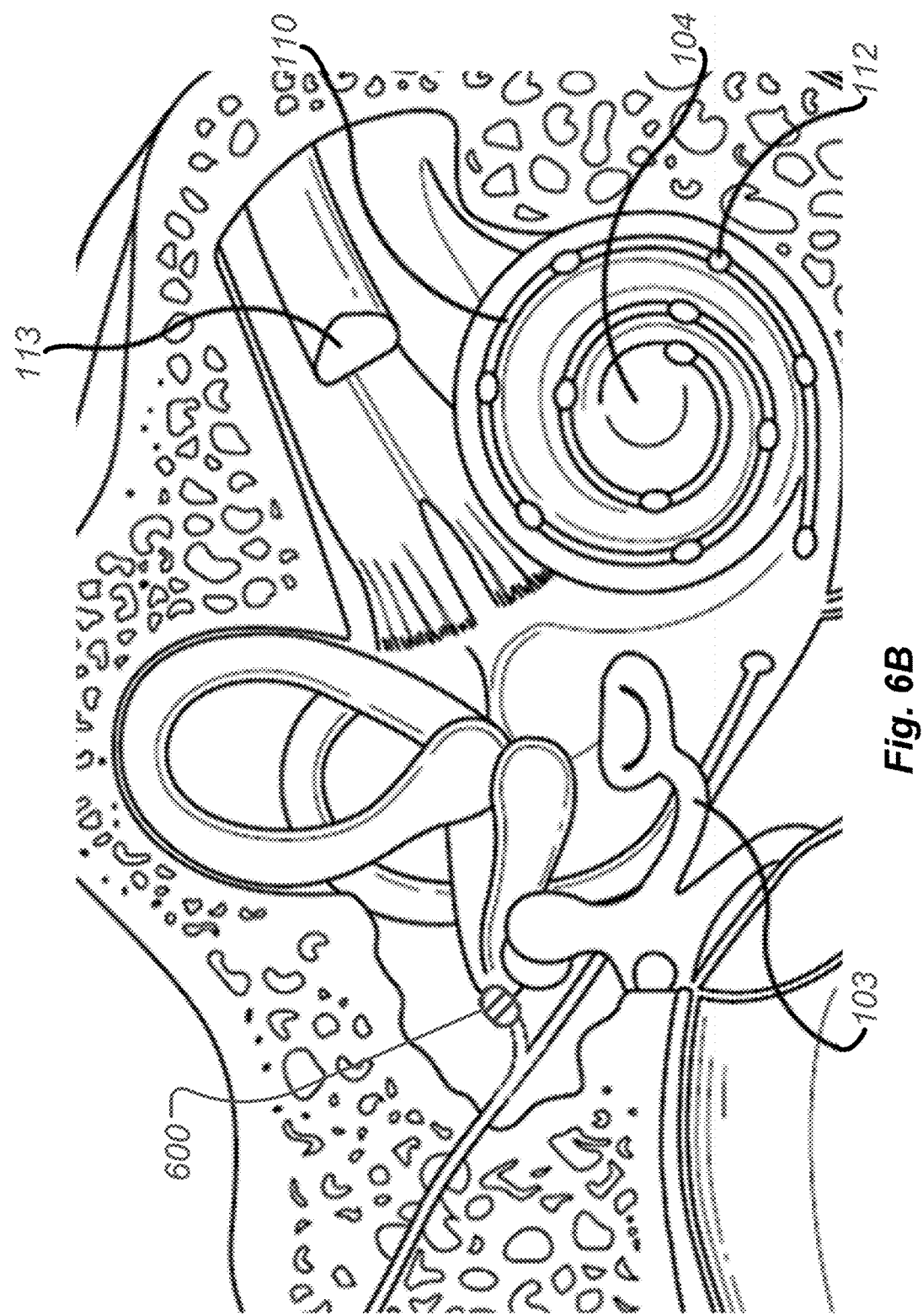
Figure 6C:
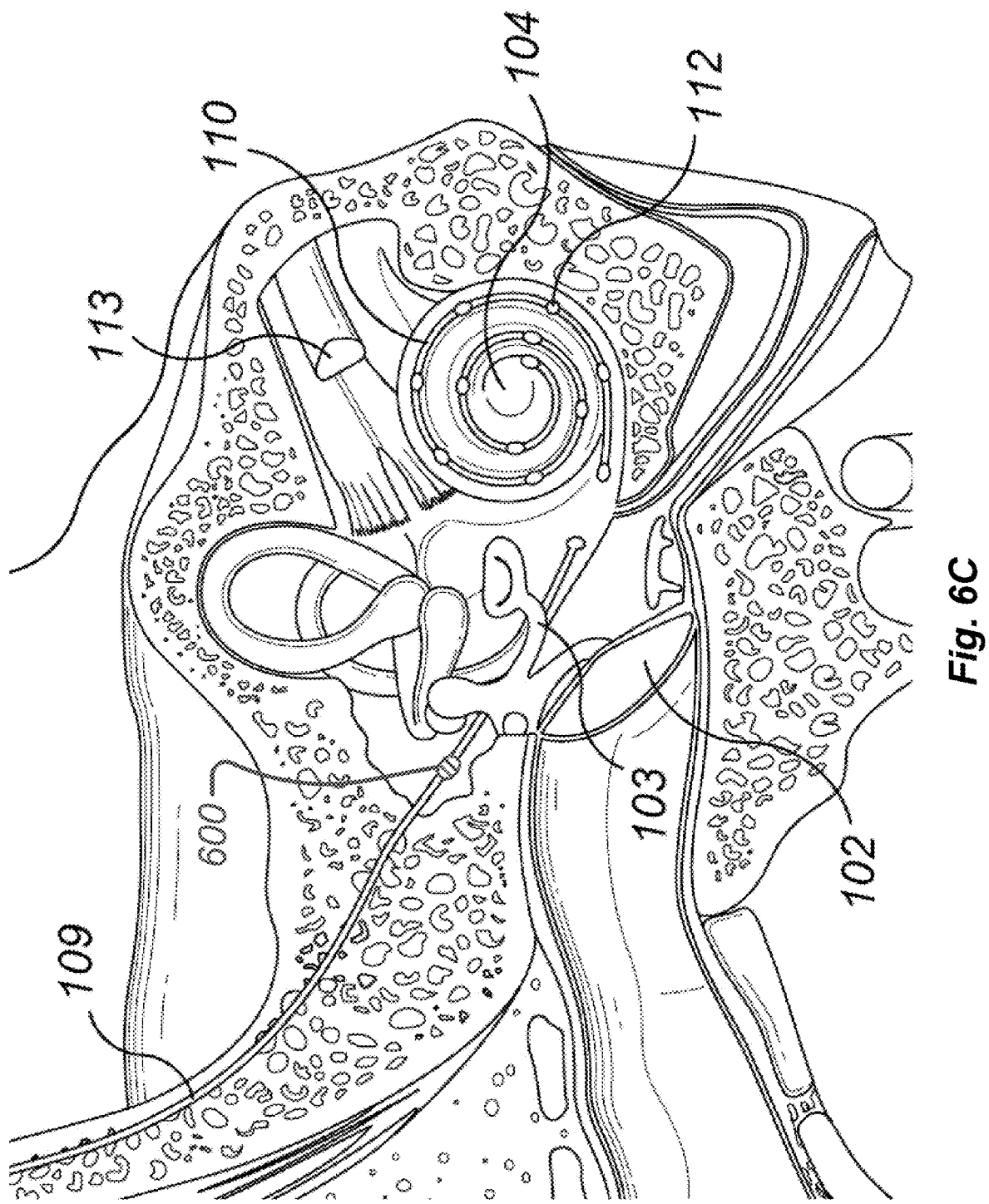

FIG. 6A-6C shows various specific response sensor arrangements for measuring the stapedius reflex response in the middle ear of a patient with a cochlear implant according to embodiments of the present invention. In FIG. 6A, the response sensor 600 is a sensing microphone configured to sense the pressure response characteristics via diffusion sensing of the free space of the middle ear. In such an embodiment, the response sensor 600 may specifically be, for example, a MEMS microphone or a piezoelectric microphone. In the embodiment shown in FIG. 6A, the response sensor 600 branches off from the main body of the electrode lead on a separate stalk. FIG. 6C shows another embodiment with a response sensor 600 in the form of a sensing microphone that is integrated onto the outer surface of the electrode lead in the middle ear. Alternatively, instead of a sensing microphone, FIG. 6B shows an embodiment that uses a pressure sensor as the response sensor 600 that is directly engaged in contact with the ossicles so as to sense the changing response characteristics directly via conduction sensing of the ossicles as they are clamped by the stapedius reflex.

It will be appreciated that sensing the response characteristics via diffusion using a sensing microphone requires that the middle ear effectively be a closed volume. This may limit the potential for measurements during the surgical placement of the cochlear implant elements (i.e. to check if the electrode array is well placed). But this can be addressed by temporarily blocking the surgical opening of the middle ear (e.g. using Gelfoam) to allow measurements during the surgery.

As mentioned above, a pressure sensor could also be placed in the inner ear and an according pressure in the inner ear will then be sensed. This pressure is caused by fluctuations of the endolymph and/or perilymph fluid. This sensor could be within the body of the electrode array or in a separate branch.

In addition, glue ear and other ossicular discontinuities and structural problems may pose a problem (as also is the case for conventional measurements using tympanometry). This may limit the usefulness of this approach in such patients.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A system for fitting a cochlear implant to a recipient patient, the cochlear implant including an implanted electrode array with a plurality of stimulation contacts for delivering electrical stimulation signals to adjacent cochlear neural tissue, the system comprising:
   means for delivering to an ear of the patient an acoustic stimulus over a range of acoustic frequencies;
   means for measuring a baseline acoustic transfer function to the acoustic stimulus using a response sensor configured to sense pressure response characteristics in the middle or inner ear;
   means for determining a maximum comfortable level (MCL) of stimulation for at least one stimulation contact in the electrode array, based on performing an electrically evoked measurement comprising:
   i. delivering an electric stimulation signal at a given stimulus intensity to the at least one stimulation contact,
   ii. using the response sensor to measure a modified acoustic transfer function to the electric stimulation signal,
   iii. comparing the modified acoustic transfer function to the baseline acoustic transfer function to determine when a stapedius reflex response occurs,
   iv. when the stapedius reflex response does not occur, increasing the stimulus intensity and repeating the electrically evoked measurement, and
   v. when the stapedius reflex response occurs, identifying the MCL for the at least one stimulation contact based on the corresponding stimulus intensity.

2. The system according to claim 1, wherein the response sensor is configured to sense the pressure response characteristics via diffusion sensing.

3. The system according to claims 1, wherein the response sensor is a sensing microphone.

4. The system according to claim 1, wherein the response sensor is configured to sense the pressure response characteristics via conduction sensing.

5. The system according to claim 1, wherein the pressure response characteristics include sound level and frequency response.

6. A computer program product encoded in a non-transitory computer-readable medium for fitting a cochlear implant to a recipient patient, the cochlear implant including an implanted electrode array with a plurality of stimulation contacts for delivering electrical stimulation signals to adjacent cochlear neural tissue, the product comprising:

program code for delivering to an ear of the patient an acoustic stimulus over a range of acoustic frequencies;

program code for measuring a baseline acoustic transfer function to the acoustic stimulus using a response sensor configured to sense pressure response characteristics in the middle or inner ear;

program code for determining a maximum comfortable level (MCL) of stimulation for at least one stimulation contact in the electrode array, based on performing an electrically evoked measurement comprising:
  i. delivering an electric stimulation signal at a given stimulus intensity to the at least one stimulation contact,
  ii. using the response sensor to measure a modified acoustic transfer function to the electric stimulation signal,
  iii. comparing the modified acoustic transfer function to the baseline acoustic transfer function to determine when a stapedius reflex response occurs,
  iv. when the stapedius reflex response does not occur, increasing the stimulus intensity and repeating the electrically evoked measurement, and
  v. when the stapedius reflex response occurs, identifying the MCL for the at least one stimulation contact based on the corresponding stimulus intensity.

7. The product according to claim 6, wherein the response sensor is configured to sense the pressure response characteristics via diffusion sensing.

8. The product according to claim 6, wherein the response sensor is a sensing microphone.

9. The product according to claim 6, wherein the response sensor is configured to sense the pressure response characteristics via conduction sensing.

10. The product according to claim 6, wherein the pressure response characteristics include sound level and frequency response.

11. A method for fitting a cochlear implant to a recipient patient, the cochlear implant including an implanted electrode array with a plurality of stimulation contacts for delivering electrical stimulation signals to adjacent cochlear neural tissue, the method comprising:

delivering to an ear of the patient an acoustic stimulus over a range of acoustic frequencies;

measuring a baseline acoustic transfer function to the acoustic stimulus using a response sensor configured to sense pressure response characteristics in the middle or inner ear;

determining a maximum comfortable level (MCL) of stimulation for at least one stimulation contact in the electrode array, based on performing an electrically evoked measurement comprising:
  i. delivering an electric stimulation signal at a given stimulus intensity to the at least one stimulation contact,
  ii. using the response sensor to measure a modified acoustic transfer function to the electric stimulation signal,
  iii. comparing the modified acoustic transfer function to the baseline acoustic transfer function to determine when a stapedius reflex response occurs,
  iv. when the stapedius reflex response does not occur, increasing the stimulus intensity and repeating the electrically evoked measurement, and
  v. when the stapedius reflex response occurs, identifying the MCL for the at least one stimulation contact based on the corresponding stimulus intensity.

12. The method according to claim 11, wherein the response sensor is configured to sense the pressure response characteristics via diffusion sensing.

13. The method according to claim 11, wherein the response sensor is a sensing microphone.

14. The method according to claim 11, wherein the response sensor is configured to sense the pressure response characteristics via conduction sensing.

15. The method according to claim 11, wherein the pressure response characteristics include sound level and frequency response.

* * * * *